United States Patent
Kalkbrenner et al.

(10) Patent No.: US 9,201,011 B2
(45) Date of Patent: Dec. 1, 2015

(54) INCREASED DEPTH-RESOLUTION MICROSCOPY

(75) Inventors: Thomas Kalkbrenner, Jena (DE); Helmut Lippert, Jena (DE); Ingo Kleppe, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 13/885,979

(22) PCT Filed: Nov. 11, 2011

(86) PCT No.: PCT/EP2011/069918
§ 371 (c)(1),
(2), (4) Date: Jul. 30, 2013

(87) PCT Pub. No.: WO2012/065910
PCT Pub. Date: May 24, 2012

(65) Prior Publication Data
US 2013/0302905 A1   Nov. 14, 2013

(30) Foreign Application Priority Data
Nov. 16, 2010 (DE) .......................... 10 2010 044 013

(51) Int. Cl.
*G01N 21/64* (2006.01)
*G02B 21/00* (2006.01)
(Continued)

(52) U.S. Cl.
CPC ........ *G01N 21/6447* (2013.01); *G01N 21/6428* (2013.01); *G01N 21/6458* (2013.01);
(Continued)

(58) Field of Classification Search
CPC . G01N 21/64; G01N 21/6447; G02B 21/0076
USPC .......................................... 436/172; 422/82.8
See application file for complete search history.

(56) References Cited

U.S. PATENT DOCUMENTS 7,626,695 B2    12/2009  Betzig et al.
7,675,045 B1 *   3/2010  Werner et al. .............. 250/458.1
(Continued)

FOREIGN PATENT DOCUMENTS

DE    102006021317 A1    10/2007
DE    102008009216 A1     8/2009
(Continued)

OTHER PUBLICATIONS

Betzig et al.: "Imaging Intracellular Fluorescent Proteins at Nanometer Resolution", Science 313, 1642, 2006, 1642-1645.
(Continued)

*Primary Examiner* — Christopher A Hixson
*Assistant Examiner* — Emily Berkeley
(74) *Attorney, Agent, or Firm* — Patterson Thuente Pedersen, P.A.

(57) ABSTRACT

A method for high-resolution luminescence microscopy of a sample marked with marking molecules that can be activated to excite particular luminescent radiation, including: repeated activation of a subset of the marking molecules to emit luminescent radiation; repeated imaging of the sample along a depth direction and with a predetermined optical resolution; and producing images from the repeated imaging. Locations of the marking molecules are determined with a spatial resolution that is increased above the predetermined optical resolution. Activation of the marking molecules can be through radiation introduced into multiple regions, each extending along a plane substantially perpendicular to the depth direction. The regions can be arranged so that the regions are behind one another and overlap only partially. Separate images of the sample may be recorded for activation in each of the regions in order to obtain depth information relating to the marking molecules from the separate images.

10 Claims, 8 Drawing Sheets

(51) Int. Cl.
  *G02B 21/16* (2006.01)
  *G02B 21/36* (2006.01)
  *G02B 27/58* (2006.01)

(52) U.S. Cl.
  CPC ............ *G02B21/0076* (2013.01); *G02B 21/16* (2013.01); *G02B 21/367* (2013.01); *G02B 27/58* (2013.01); *G01N 21/64* (2013.01)

(56) References Cited

U.S. PATENT DOCUMENTS

| | | | |
|---|---|---|---|
| 2006/0012864 A1* | 1/2006 | Funk et al. | 359/385 |
| 2006/0033987 A1* | 2/2006 | Stelzer et al. | 359/385 |
| 2009/0134342 A1 | 5/2009 | Hell et al. | |
| 2010/0062460 A1 | 3/2010 | Pande et al. | |
| 2010/0160613 A1 | 6/2010 | Seyfried et al. | |
| 2010/0207037 A1 | 8/2010 | Tearney et al. | |
| 2010/0265318 A1 | 10/2010 | Bewersdorf et al. | |
| 2010/0283835 A1 | 11/2010 | Bewersdorf et al. | |
| 2011/0031414 A1* | 2/2011 | Lippert et al. | 250/459.1 |
| 2011/0036996 A1 | 2/2011 | Wolleschensky et al. | |
| 2011/0043619 A1* | 2/2011 | Wolleschensky | 348/79 |
| 2011/0160083 A1 | 6/2011 | Hell et al. | |

FOREIGN PATENT DOCUMENTS

| | | | |
|---|---|---|---|
| DE | 102008024568 A1 | 12/2009 | |
| JP | 2008/197443 | 8/2008 | |
| JP | 2010-092002 | 4/2010 | |
| WO | WO 2006/127692 A2 | 11/2006 | |
| WO | WO 2007/009812 A1 | 1/2007 | |
| WO | WO 2009/085218 A1 | 7/2009 | |
| WO | WO 2009/100830 A1 | 8/2009 | |
| WO | WO 2009124700 A1 * | 10/2009 | G01J 1/58 |
| WO | WO 2009/132811 A1 | 11/2009 | |
| WO | WO 2009132811 A1 * | 11/2009 | H04N 7/18 |

OTHER PUBLICATIONS

Durst et al.: "Simultaneous spatial and temporal focusing for axial scanning", Optics Express, vol. 14, No. 25, Dec. 11, 2006, 3285-3290.

Egner et al.: "Fluorescence Nanoscopy in Whole Cells by Asynchronous Localization of Photoswitching Emitters", Biophysical Journal, vol. 93, Nov. 2007, 3285-3290.

Hess et al.: "Dynamic clustered distribution of hemagglutinin resolved at 40 nm in living cell membranesdiscriminates between raft theories", PNAS, vol. 104, No. 44, Oct. 30, 2007, 17370-17375.

Hess et al.: "Ultra-High Resolution Imaging by Fluorescence Photoactivation Localization Microscopy",Biophysical Journal, vol. 91, Dec. 2006, 4258-4272.

Huang et al.: ‚Three-Dimensional Super-Resolution Imaging by Stochastic Optical Reconstruction Microscopy, Science Express, Jan. 3, 2008, 1-7.

Huang et al.: "Supporting Online Material for Three-Dimensional Super-Resolution Imaging by Stochastic Optical Reconstruction Microscopy", Science Express, Jan. 3, 2008, 1-8.

Juette et al.: ‚Three-dimensional sub-1 00 nm resolution fluorescence microscopy of thick samples, Nature Methods, vol. 5, No. 6, Jun. 2008, 527-529.

Juette et al.: "Supplementary figures and text for Three-Dimensional sub-1 00 nm resolution fluorescence microscopy of thick samples", Nature Methods, vol. 5, No. 6, Jun. 2008, 1-11.

Lessard et al.: "Three-dimensional tracking of individual quantum dots", Applied Physics Letters 91, 2007, 3 pages.

Pavani et al.: "Three-dimensional, single-molecule fluorescence imaging beyond the diffraction limit by using a double-helix point spread function", PNAS, vol. 1 06, No. 9, Mar. 3, 2009, 2995-2999.

Rust et al.: "Sub-diffraction-limit imaging by stochastic optical reconstruction microscopy (STORM)", Nature Methods, Aug. 9, 2006, 1-3.

Schroff et al.: "Dual-color super resolution imaging of genetically expressed probes within individual adhesion complexes", PNAS, vol. 104, No. 51, Dec. 18, 2007, 20308-20313.

Shtengel et al.: ‚Interferometric fluorescent super-resolution microscopy resolves 3D cellular Ultra structure, PNAS, vol. 106, 1-6.

Shtengel et al.: "Supporting Information". PNAS, vol. 106, 1-7.

Toprak et al.: ‚Three-Dimensional Particle Tracking via Bifocal Imaging, Nano Letters 2007. vol. 7,No. 7, 2043-2045.

Fahrbach et al.: ‚A line scanned light-sheet microscope with phase shaped self-reconstructing beams,Optics Express, vol. 18, No. 23, Nov. 8, 2010. 1-16.

Gurskaya et al.: "Engineering of a monomeric green-to-red photoactivatable fluorescent protein induced by blue light", Nature Biotechnology, vol. 24, No. 4, Apr. 2006, 461-465.

Keller et al.: ‚Quantitative in vivo imaging of entire embryos with Digital Scanned Laser Light Sheet Fluorescence Microscopy, Current Opinion in Neurobiology 2009, vol. 19, 1-9.

* cited by examiner

INCREASED DEPTH-RESOLUTION MICROSCOPY

RELATED APPLICATIONS

The present application is a National Phase entry of PCT Application No. PCT/EP2011/069918, filed Nov. 11, 2011, which claims priority from DE Patent Application No. 10 2010 044 013.2, filed Nov. 16, 2010, which applications are hereby incorporated by reference in their entireties.

FIELD OF THE INVENTION

The invention relates to a method for high-resolution luminescence microscopy of a sample, which is marked with marking molecules which can be activated in such a manner that, once activated, they can be excited to emit particular luminescent radiation, wherein the method has the following steps:
a) repeated activation and excitation of a subset of the marking molecules present in the sample to emit luminescent radiation, wherein, in the sample, at least some of the luminescent marking molecules are at least at a distance from the luminescent marking molecules immediately adjacent thereto, which distance is greater than or equal to a length which results from a predetermined optical resolution,
b) repeated imaging of the sample with luminescent marking molecules along a depth direction and with the predetermined optical resolution, and
c) production of individual images from the imaging operations from step b), wherein the geometrical locations of the luminescent marking molecules in the individual images are determined with a spatial resolution which is increased above the predetermined optical resolution.

The invention additionally relates to a microscope for high-resolution luminescence microscopy of a sample, which is marked with marking molecules which can be activated in such a manner that, once activated, they can be excited to emit particular luminescent radiation, wherein the microscope has:
a) an illumination beam path, adapted for repeated activation and excitation of a subset of the marking molecules present in the sample to emit luminescent radiation in such a manner, wherein, in the sample, at least some of the luminescent marking molecules are at least at a distance from the luminescent marking molecules immediately adjacent thereto, which distance is greater than or equal to a length which results from a predetermined optical resolution,
b) an imaging device, adapted for repeated imaging of the sample with luminescent marking molecules along a depth direction and with the predetermined optical resolution, and
c) a control and evaluation device, which produces individual images from the imaging operations and determines the geometrical locations of the luminescent marking molecules in the individual images with a spatial resolution which is increased above the predetermined optical resolution.

BACKGROUND OF THE INVENTION

In the state of the art, various methods have been developed to break the diffraction limit in luminescence microscopy. For the purpose of examining biological specimens, in luminescence microscopy, particular dyes (so-called phosphors or fluorophores) are used for specific marking of samples, e.g. cell parts. The sample is illuminated with illumination radiation, which acts as excitation radiation, and the luminescent radiation thus excited is detected by means of suitable detectors. Usually, for this purpose, a dichroic beam splitter is provided in the microscope, in combination with block filters, which separate off the luminescent radiation from the excitation radiation and enable separate observation. This procedure makes it possible to represent individual, differently coloured cell parts in the microscope. Naturally, several parts of a specimen can also be dyed at the same time with differing dyes that attach specifically to differing structures of the specimen. This method is referred to as multiple luminescence. It is also possible to measure samples that are luminescent per se, i.e. without the addition of dye.

Luminescence is understood here, as is common generally, as a generic term for phosphorescence and fluorescence, i.e. it includes both processes. Insofar as reference is made here to fluorescence, that is to be understood as pars pro toto and non-limiting.

A method that achieves a resolution beyond the diffraction limit is known from WO 2006127692 or DE 102006021317 A1. This method, known by the abbreviation PALM (Photo Activated Light Microscopy), uses a marking substance that can be activated by means of optical radiation. It is only in the activated state that the marking substance can then be excited to emit particular fluorescent radiation. Non-activated molecules of the marking substance emit no fluorescent radiation, or at least no appreciable fluorescent radiation, even after introduction of excitation radiation. The activation radiation thus brings the marking substance into a state in which it can be excited to fluorescence. Other types of activation, e.g. of a thermal nature, are also possible. The general term switching signal is therefore used. In the PALM method, then, the switching signal is applied such that at least a certain proportion of the activated marking molecules are at such a distance from adjacent activated molecules that, measured at the optical resolution of the microscopy, they are separate or subsequently separable. The activated molecules are thus at least largely isolated. After recording of the luminescent radiation, the centre of the radiation distribution attributable to resolution limitation is then ascertained for these isolated molecules and, from this, the position of the molecules is determined by computation, with a greater accuracy than is actually afforded by the optical imaging. This increased resolution, through computational centroid determination of the diffraction distribution, is also referred to in the English-language specialist literature as "superresolution". It requires that, in the sample, at least some of the activated marking molecules be distinguishable, i.e. isolated, with the optical resolution with which the luminescent radiation is detected. For such molecules, specification of the location can then be achieved with increased resolution.

For the purpose of isolating individual marking molecules, the PALM method makes use of the fact that the probability with which a marking module is activated after receiving the switching signal of given intensity, e.g. one photon of the activation radiation, is the same for all molecules. Concerning the intensity of the switching signal, and therefore the number of photons, incident on a unit of area of the sample, it can thus be ensured that the probability of activating marking molecules present in a given surface region of the sample is so low that there are sufficient regions in which only distinguishable marking molecules emit fluorescent radiation within the optical resolution. Through appropriate selection of the intensity, e.g. the photon density, of the switching signal, the result achieved is that, insofar as possible, only marking molecules that are isolated, in terms of the optical resolution, are activated and subsequently emit fluorescent radiation. The determination of location is effected by means of high-sensitivity cameras in wide-field operation with an accuracy down to the nanometer range, if sufficient photons of the isolated marking molecules can be detected. The quasi-punctiform light source, which is constituted by a luminescent marking molecule, is imaged to several camera pixels by the point spread function of the microscope, and the exact position of the luminescent marking molecule in the sample plane assigned to the camera plane can be determined, for example, by fitting the known point spread function (e.g. by means of a Gaussian fit) or centroid determination, etc. Localization accuracies of between 5 and 30 nm are thereby achieved. For localization, various image evaluation methods are known. For this, reference is made, by way of example, to DE 102008009216 A1. For the purpose of imaging the entire sample, the isolation of the marking molecules of the subset by introduction of the activation radiation, subsequent excitation and fluorescent radiation imaging is repeated until, insofar as possible, all marking molecules have been included once in a subset and isolated within the resolution of the imaging operation.

The PALM method has the advantage that a high spatial resolution is not required, either for the activation or for the excitation. Instead, both the activation and the excitation can be effected in wide-field illumination. Individual variants of the PALM method differ principally in the choice of fluorophores and in the type of optical switching process. In the case of molecules that are activated by a separate activation radiation such that they can be excited, the isolation can be effected through suitable application of the activation radiation. Also known, however, are approaches in which, for example, selective bleaching of the sample is used for isolation.

However, this localization accuracy is achieved only laterally, i.e. in a plane assigned to the image plane of the camera. In this respect, the methods are thus limited to a two-dimensional sample analysis. Approaches for localizing luminescent marking molecules in the third spatial direction, which, in relation to the imaging of the sample, is the depth direction, are likewise known from the state of the art.

The publication Huang et al., Science 319, page 810, 2008, proposes introducing into the imaging beam path a low-power cylindrical lens, which results in an astigmatic point spread function. Accordingly, the image of the molecule on the camera is distorted elliptically as soon as the molecule is located above or below the point of symmetry of the point spread function. The information concerning the depth position of the luminescent marking molecule can be obtained from the orientation and the strength of the distortion. A disadvantage of this method is that the local environment and the orientation of a molecular dipole can also result in a distortion of the image of the luminescent marking molecule that has nothing to do with the depth position. An incorrect depth value is then assigned to such luminescent marking molecules, according to their orientation.

The publication Pavani et al., PNAS 106, page 2995, 2009, proposes modifying the point spread function by a spatial phase modulator in the imaging operation to a double helix structure. The point images of individual luminescent marking molecules then become double spots, their depth position being coded in the angular orientation of the common axis of the double spot.

The publication by Shtengel et al., PNAS 106, page 3125, 2009, proposes causing the photons emitted by the luminescent marking molecules to be self-interfering. Used for this purpose are two objective lenses, mounted in 4π configuration, which simultaneously observe the luminescent marking molecules. The partial beam paths obtained in such a manner are brought to a state of interference by means of a special three-way beam splitter. Each of the three-point images received as a result is detected by a camera. The intensity ratios of the three-point images provide an indication of the depth position.

The publications Toprak et al., Nanolet. 7, pages 3285-3290, 2007, and Juette et al., Nature Methods 5, page 527, 2008, describe an approach in which a 50/50 beam splitter is built into the imaging beam path, which beam splitter splits the image of the sample into two sub-images. These two images are detected independently. In addition, in one of the partial beam paths obtained thereby, an optical path-length difference is introduced in such a manner that two object planes, lying apart by approximately half or the entirety of the minimum optical resolution (for example 700 nm) in the z direction, i.e. depth direction, are produced from the two partial beam paths. The depth position of marking molecules that lie between these two planes is then obtained through subtraction of the two sub-images of the same marking molecule, or through corresponding fitting of a three-dimensional point spread function. This method requires two high-sensitivity cameras, or two images have to be arranged next to each other on the receiving region of a high-sensitivity camera, which naturally results in a limitation of the image field. For both options, moreover, a precise adjustment of the beam paths and calibration measurements are essential, in order to achieve a superimposition of the two sub-images that has sub-pixel precision. Furthermore, the two sub-images of a marking molecule generally differ in shape, since the lateral extent of the point spread function of an imaging system changes depending on the position of the object plane observed.

SUMMARY OF THE INVENTION

The invention is therefore based on the object of developing a method for the high-resolution microscope such that, while avoiding the stated disadvantages of the state of the art, a high resolution is achieved in the depth direction.

This object is achieved by a method of the type named at the outset, in which, for high resolution along the depth direction, d) the activation and/or excitation in the steps a) is/are effected with radiation which is introduced into at least two regions, wherein the regions each extend along a plane which is substantially perpendicular to the depth direction, the regions have a predetermined extent in the depth direction, and the regions are arranged in such a manner that said regions are, when seen in the depth direction, behind one another and overlap only partially, and e) separate images of the sample are recorded in the steps b) for activation and/or excitation of each of the at least two regions in order to obtain depth information relating to the luminescent marking molecules from the separate images.

The object is further achieved by a microscope of the type named at the outset, in which, for high resolution along the depth direction, d) the illumination beam path introduces the activation and/or excitation radiation into at least two regions, wherein the regions each extend along a plane which is substantially perpendicular to the depth direction, the regions have a predetermined extent in the depth direction, and the regions are arranged in such a manner that said regions are, when seen in the depth direction, behind one another and overlap only partially, and e) the imaging device records separate images of the sample for activation and/or excitation of each of the at least two regions and the control and evaluation device obtains a depth information relating to the luminescent marking molecules from the separate images.

The invention thus departs from the procedure of the state of the art, which universally effects an intervention in the detection process in order to determine the depth position, i.e. the z position, of the marking molecules. Now, according to the invention, suitable action is made in the excitation and/or activation process in order to achieve a localization in respect of the depth position. Depending on the fluorophore used, the excitation or activation radiation, or a radiation that effects both, is introduced accordingly. In the description that follows, reference is made, purely by way of example, to some extent, to the excitation radiation. The statements made are equally applicable, however, to the activation radiation or to a radiation that effects both activation and excitation.

In the concept according to the invention, the radiation illuminates in two states, to each of which there is assigned a region that is arranged in a plane lying transversely in relation to the depth direction. The respective region can also include only a sub-region of the plane. The regions are at least partially behind one another and overlap only partially. Separate images of the two regions are recorded. Only marking molecules that are located in the overlap region between first and second region appear in both images. Consequently, the spatial resolution in the depth direction can be reduced to the size of the overlap region. Since, in the recording of images from both regions, there is no alteration of a detection beam path, the images alter only in respect of their intensity, and not in respect of their shape.

The image separation can be produced through suitable modulation of the illumination of the regions, e.g. through an alternating illumination.

The overlap of the regions that are located behind one another in the depth direction is decisive for the resolution in the depth direction. Depending on the optical design, the delimitation of the extent of the regions in the depth direction differs in sharpness. If, for example, diffraction-limited radiation is introduced in the form of a light sheet, the thickness of the light sheet, i.e. its extent in the depth direction, depends on the introducing optics. The light intensity follows, for example, a Gaussian function in the z direction. The spatial extent can then be defined on the basis of a value at which the light intensity has decreased to a particular minimum value. A usual value in this case is the 1/e value. However, other definitions are possible within the scope of the invention.

The size of the overlap region affects the resolution in the depth direction. For this reason, it is preferred to select a measure of the overlap region in the depth direction, in dependence on a density of the marking molecules in the sample. In this case, imaging of the samples in the conventional sense, i.e. without increased depth resolution, can be performed first, in order to determine the density of the marking molecules in the sample. The overlap is then selected as appropriate, for example by consultation of previously determined tabular values, and set.

For the increase in resolution in the depth direction according to the invention, it is important that the regions are located at least partially behind one another and partially overlap, and that the regions are irradiated to be distinguishable in detection.

The radiation can be introduced in the form of a light sheet lying transversely in relation to the depth direction. It is possible for a light sheet to be displaced, transversely in relation to the depth direction, into at least two positions, such that the light sheet in one position has a region of overlap with the light sheet in the other position. The displacement is thus less than half the thickness of the light sheet. Alternatively, it is also possible to use two light sheets, which are located in relation to each other such that they overlap in the depth direction. It is then possible to switch between these two light sheets, i.e. the light sheets are switched on and off alternately, or the light sheets are differentially modulated. A light sheet in this case can also be understood to be an arrangement in which a light-sheet plane is scanned by a light beam during the detection period, such that a quasi-light-sheet illumination is created by the movement in relation to time. The scanning takes place at a faster speed than the time resolution of the detection process.

By a "light sheet" is meant here, inter alia, that the illumination is introduced at an angle in relation to the detection axis z. Normally, the illumination region comprises the region of the detection plane that is predefined by the detection optics. The illumination can be effected both parallelwise, e.g. by means of anamorphotic optics, and sequentially, through scanning by means of an excitation beam. The combination of both variants is also possible. Also included in the meaning of the invention presented here are variants in which the excitation region only partially includes the detection plane, e.g. through introduction of only one line longitudinally in relation to the detection plane, or through introduction of a light sheet at an angle in relation to the detection plane, or a combination of such variants. Various possibilities for light-sheet production are described in P. Keller and E. Stelzer, "Quantitative in vivo imaging of entire embryos with Digital Scanned Laser Light Sheet Fluorescence Microscopy", Current Opinion in Neurobiology, 2009, vol. 19, pages 1-9, the disclosure of which, in this respect, is to be included here in its entirety by reference.

The introduction, according to the invention, of the excitation and/or activation radiation into two depth regions that are located behind one another, overlap and are irradiated to be distinguishable in detection, can also be achieved in that the radiation is not introduced transversely in relation to the depth direction, as in the case of a light sheet, but along the depth direction. If radiation is focussed into the sample, an excitation and/or activation are/is produced only in a small volume region. This focus region is then delimited not only laterally, but also in the depth direction. If two such focus regions are placed behind one another, two regions are likewise obtained which enable the concept according to the invention to be realized. In order to effect wide-field illumination of the entire sample, it is possible to displace the two foci along the respective focal plane (transversely in relation to the depth direction). If such a displacement is performed sufficiently rapidly, each region per se is illuminated with excitation and/or activation radiation in a time period that is short in comparison with the duration of the luminescence excited thereby. This results, again, in two regions that are behind one another in the depth direction and that overlap by a certain amount. The displacement of the foci along the respective plane can be achieved most simply in that a rotating disc is used in the introduction of the excitation and/or activation radiation, on which disc there are microlenses that have differing focal lengths, corresponding to the staggered arrangement of the two regions behind one another.

If a two-photon process is used for excitation and/or activation, the intensity distribution in the depth direction is particularly sharp, and gives a particularly good high resolution.

Insofar as the invention is described above or in the following with reference to a method, this disclosure applies equally to a corresponding microscope having suitable means and, in particular, a suitable control and evaluation device for executing the method. Conversely, a description of a corresponding microscope equally discloses corresponding method steps according to the mode of operation thereof.

It is understood that the features mentioned above and those yet to be explained in the following are applicable, not only in the stated combinations, but also in other combinations or singly, without departure from the scope of the present invention.

BRIEF DESCRIPTION OF THE DRAWINGS

The invention is explained by way of example in yet more detail in the following with reference to the attached drawings, in which.

DETAILED DESCRIPTION

Figure 1:
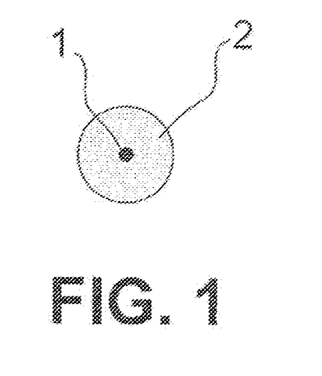
FIG. 1 is a schematic representation of an activated marking molecule in a resolution-limited volume.

Shown schematically in FIG. 1 is a marking molecule 1 that has been excited to fluorescence. Naturally, fluorescence detection requires a large number of excitations, since each excitation delivers exactly one fluorescence photon, and the detection of radiation requires integration of many fluorescence photons. On the basis of physical principles, the fluorescent radiation emitted by the marking molecule 1 can be detected only with a limited optical resolution in a microscope. Even if the microscope achieves the diffraction limit of the optical resolution, the photons of the fluorescent marking molecule 1 are still scattered because of diffraction, and are therefore detected in a diffraction disc 2. Thus, in principle, instead of representing the geometrical extent of the marking molecule 1, which in FIG. 1 is indicated schematically as a black circle, the microscope represents a larger object, which in FIG. 1 is illustrated by the diffraction disc 2. The size of the diffraction disc 2 depends on the quality of the microscopy equipment used, and is defined by the half width of the point spread function of the optical imaging. In actuality, naturally, the object is not a two-dimensional object, but a diffraction volume into which the fluorescence photons pass. In the two-dimensional representation of FIG. 1, however, this appears as a disc. For this reason, the term diffraction disc is taken here very generally for a maximum resolution volume that can be achieved by the optics used. However, the optics used need not necessarily operate at the diffraction limit, even if this is to be preferred.

To then enable the marking molecule 1 to be localized with greater precision within the diffraction disc 2, the PALM method, already outlined in general terms above, is used. This activates individual marking molecules, wherein, in this description, the term activation means, very generally, the activation of particular luminescence properties of the marking molecules, i.e. both a switching-on of the luminescence excitation capability and an alteration of the luminescence emission spectrum, which corresponds to the switching-on of particular luminescence properties. In the embodiment example described here, the activation is effected by optical activation radiation. Also possible, however, are other, non-optical activation mechanisms.

The activation is then effected such that there are at least some activated molecules the centroid of which is not located in the diffraction disc of other activated molecules, i.e. which are at least still just distinguishable within the optical resolution.

Figure 2:
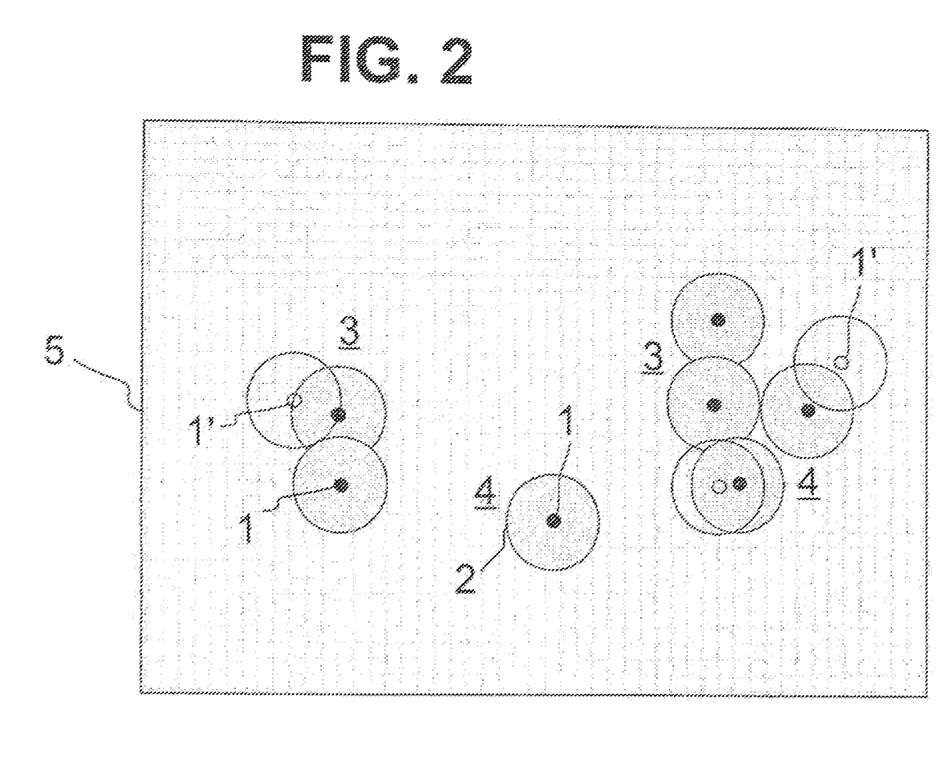
FIG. 2 is a schematic representation of the imaging of various activated and non-activated marking molecules on a spatial-resolution detector.

Shown schematically in FIG. 2 is an exemplary situation on a detector 5, which integrates the photons with spatial resolution. As can be seen, there are regions 3 in which the diffraction discs of adjacent marking molecules overlap. In this case, however, as can be seen in the region 3 on the left in FIG. 2, only those marking molecules that have been activated beforehand are relevant. Non-activated marking molecules 1' do not emit the particular fluorescent radiation that is picked up on the matrix detector 5, and thus are of no significance.

In the regions 4, e.g. in the region 4 located in the centre of the matrix detector 5, marking molecules 1 are located such that their diffraction disc 2 does not overlap with a diffraction disc of another activated marking molecule 1. The region on the right in the matrix detector 5 shows that regions 3 in which diffraction discs of activated marking molecules overlap can indeed be adjacent to regions 4 in which this is not the case. The region 4 on the right additionally illustrates that the adjacency of an activated marking molecule 1 to a non-activated marking molecule 1' is of no significance for detection, since such a marking molecule 1' does not actually emit the fluorescent radiation detected by the matrix detector 5, i.e. does not fluoresce.

Figure 3:
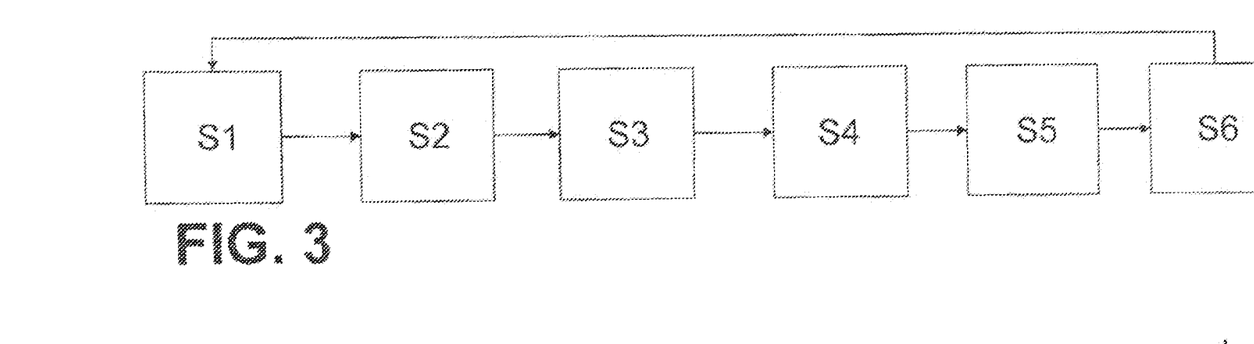
FIG. 3 is a flow diagram for image production in the PALM method.

For the purpose of recording an image with detail beyond the optical resolution predefined by the apparatus, which image is a high-resolution image within the meaning of this description, the steps represented schematically in FIG. 3 are now used.

In a first step S1, a switching signal is used to activate a subset of the marking molecules; they are thus switched from a first state, in which they cannot be excited to emit the particular fluorescent radiation, to a second state, in which they can be excited to emit the particular fluorescent radiation. Naturally, the activation signal can also effect a selective deactivation, i.e. in step S1 an inverse procedure can also be used. It is important that, after step S1, only a subset of the marking molecules can be excited to emit the particular fluorescent radiation. The activation or deactivation (for simplification only the case of activation is described in the following) is effected in dependence on the marking molecules used. In the case of a dye such as, for example, DRONPA, PA-GFP or reversibly switchable, synthetic dyes (such as Alexa/Cyan constructs), the activation is effected by optical radiation, i.e. the switching signal is switching radiation.

Figure 4:
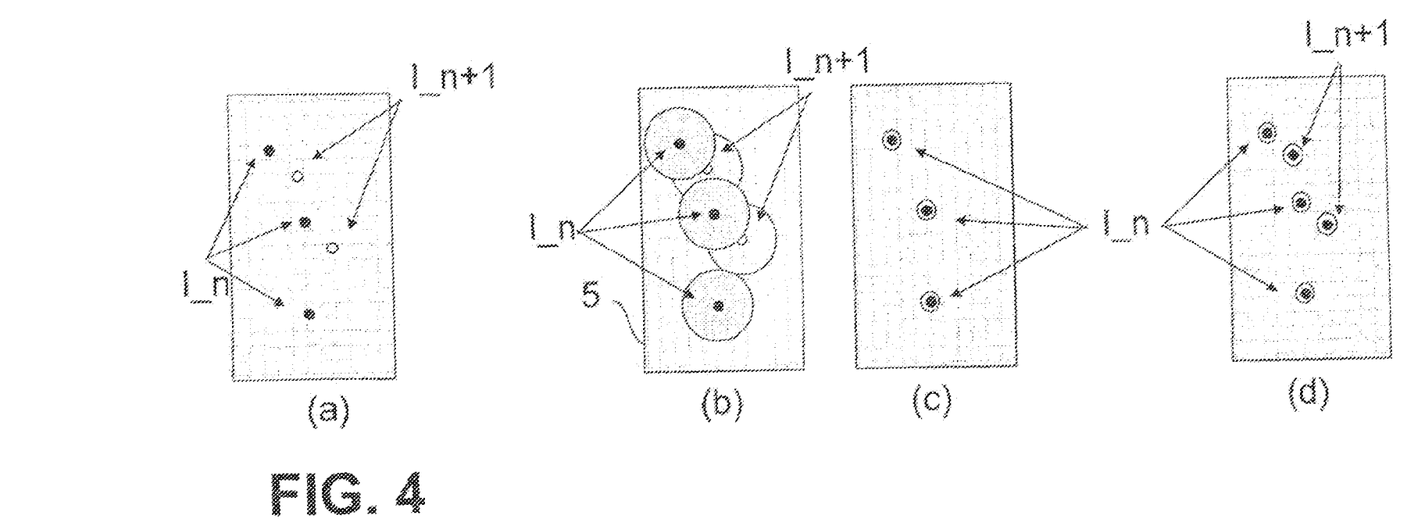
FIG. 4 depicts explanatory representations, pertaining to the flow diagram of FIG. 3, of marking molecules imaged onto the detector of FIG. 2.

The FIG. 4 represented below FIG. 3 shows, in sub-figure a, the state after step S1. Only a subset of the marking molecules 1_n has been activated. The marking molecules of this subset are represented by a full black dot. The remainder of the marking molecules have not been activated in this step. In sub-figure a of FIG. 4, they are denoted by 1_n+1.

Marking molecules that have been activated can then be excited, in a second step S2, to emit fluorescent radiation. Fluorescent proteins known from the state of the art, such as PA-GFP, or also DRONPA, are preferably used as fluorescent dyes. In the case of such molecules, activation is effected by means of radiation in the region of 405 nm, the excitation to fluorescent radiation is effected at a wavelength of approximately 488 nm, and the fluorescent radiation is in a range above 490 nm.

In a third step S3, the emitted fluorescent radiation is detected, for example through integration of the recorded fluorescence photons, such that the situation represented in sub-figure b of FIG. 4, lying beneath, is obtained on the matrix detector 5. As can be seen, the diffraction discs of the activated marking molecules 1_n do not overlap. The size of the diffraction discs is determined by the optical resolution of the imaging onto the matrix detector 5. Additionally indicated in sub-figure b of FIG. 4 are (theoretical) diffraction discs of fluorescent molecules that belong to the non-activated group 1_n+1. Since these non-activated marking molecules do not emit any fluorescent radiation, no fluorescent radiation present in their (theoretical) diffraction discs interferes with the detection of the fluorescent radiation of the subset 1_n of the activated marking molecules.

In order that in the subset 1_n as few diffraction discs as possible overlap such that the marking molecules are no longer distinguishable at all, the activation energy is set such that the subset 1_n makes up only a comparatively small proportion of the total quantity of marking molecules, such that, statistically, many marking molecules can be distinguished, relative to the volume that can be resolved with the optical arrangement.

In a fourth step S4, the position of the fluorescent marking molecules is determined computationally from the diffraction distribution of the fluorescent discs, as a result of which the resolution with which the position of the activated marking molecules is known is sharpened beyond the resolution of the optical arrangement, as shown by sub-figure c of FIG. 4.

As an alternative to a computational determination, it is quite possible, in principle, to amplify the recorded fluorescent radiation non-linearly and thus, with reduced outlay, to sharpen the resolution beyond that of the optical arrangement. The non-linear amplification can be described, for example, according to the function $S=A \cdot F^N$ (Equation 1) or $S=A \cdot \exp^{F/w}$ (with $w=10^{-N}$ (Equation 2)), wherein F is the amplitude of the fluorescence signal, A is a normalization factor and N is a whole number greater than 1. Particularly advantageous is a strong non-linear dependence of the parameter S on F, i.e., for example, high values for N in Equation 1 or 2. Naturally, other functions can also be used. In principle, the non-linearity is preferably selected such that the half width of the diffraction disc corresponds to a sought spatial resolution for specification of the location of the marking molecules. In addition to a non-linear amplification, a non-linear damping can also be used. In this case, fluorescence signals of low amplitude or intensity are damped, whereas strong signals remain at least largely undamped. Naturally, it is also possible to use a combination of non-linear amplification and damping.

A fifth step S5 then composes the marking molecules, the position of which has been defined, to form an individual image the spatial resolution of which has been increased beyond the optical resolution. However, it contains only information relating to the previously activated subset of the marking molecules.

In a sixth step S6, the individual image is set, in a known manner, in a complete image. The procedure then goes back to step S1, wherein the hitherto fluorescent molecules have to be deactivated again. Depending on the type of marking molecule, deactivation can be achieved through a separate radiation or through decay of the activation state. It is also possible to use excitation radiation to bleach marking molecules that have already been imaged.

With each pass, there is thus obtained a further individual image that contributes to the complete image. In the next pass, another subset of the marking molecules is activated, e.g. the subset 1_n+1 represented in FIG. 4(d).

As a result of the multiple passes through the steps S1 to S6, the complete image is built up from individual images of the individual passes that specify the locations of the marking molecules with a spatial resolution that is sharpened in comparison with the resolution of the optical imaging. Thus, as a result of a corresponding number of iterations, a high-resolution complete image is built up successively. In the case of the method, the reduction of the diffraction disc is preferably effected in all three spatial dimensions if a plurality of image stacks, spaced apart in the z direction, are recorded. The complete image then contains the specification of the location of the marking molecules in high resolution in all three spatial directions.

Figure 5:
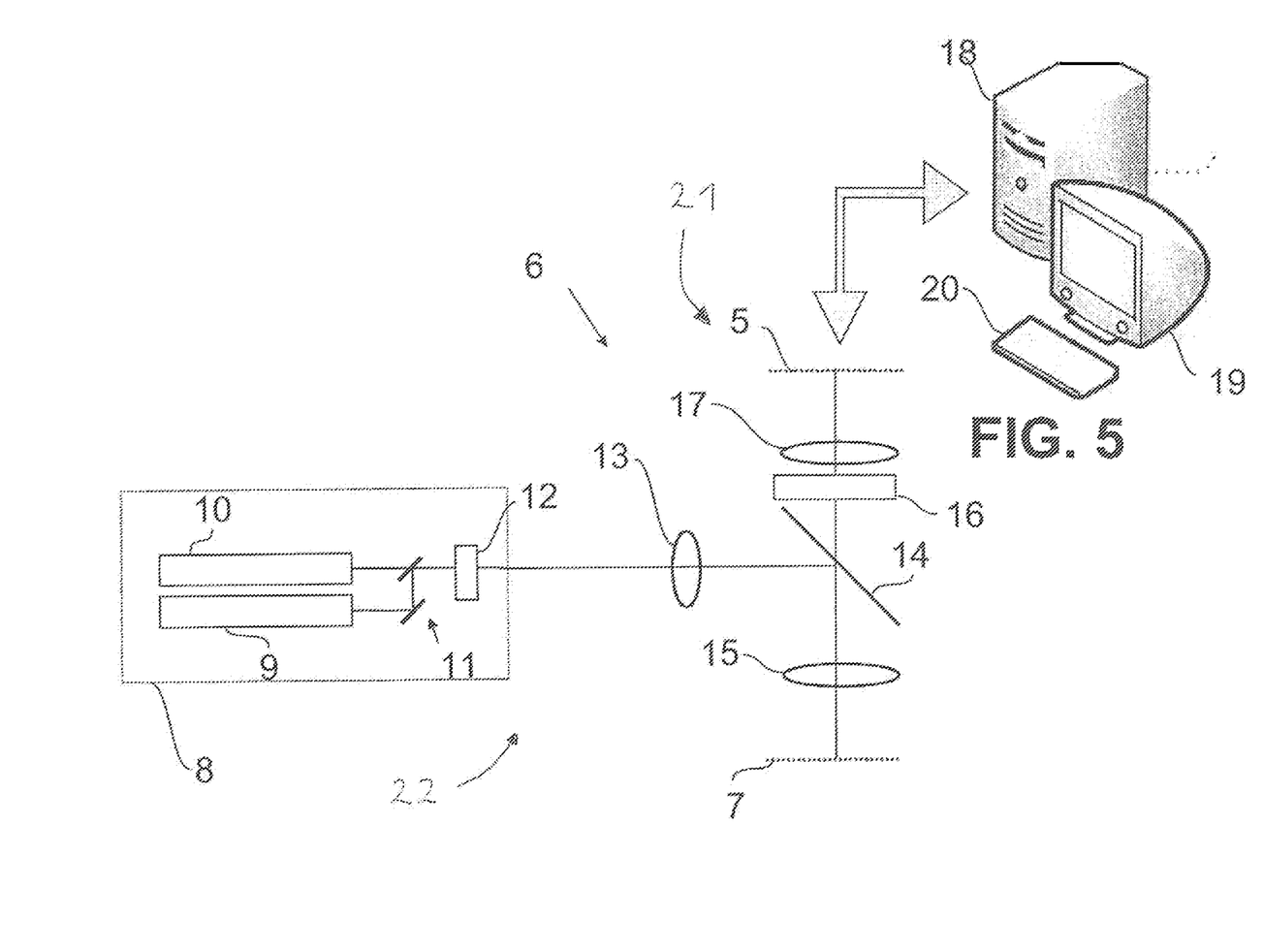
FIG. 5 is a schematic representation of a microscope for PAL microscopy.

Shown schematically in FIG. 5 is a microscope 6 for high-resolution imaging of a sample 7. The sample is marked, for example, with the dye DRONPA (cf. WO 2007009812 A1). For the purpose of activation and for fluorescence excitation, the microscope 6 has an illumination beam path 22. The latter comprises a radiation source 8, which has individual lasers 9 and 10, the beams of which are brought together by means of a beam combiner 11. The lasers 9 and 10 can emit radiation for example at 405 nm (activation radiation) and 488 nm (fluorescence excitation and deactivation). Dyes (e.g. the dye by the name of DENDRA (cf. Gurskaya et al., Nature Biotech., volume 24, pages 461-465, 2006)) are also known with which the activation and fluorescence excitation can be effected at one and the same wavelength. One laser is then sufficient.

An acousto-optic filter 12 is used for wavelength selection and for rapid switching or attenuation of individual laser wavelengths. Optics 13 focus the radiation, via a (e.g. dichroic) beam splitter 14, into a pupil of an objective lens 15, such that the radiation of the radiation source 8 is incident as wide-field illumination on the sample 7.

Fluorescent radiation generated in the sample 7 is collected, directed in a detection beam path 21. For this purpose, the beam splitter 14 is designed such that it allows the fluorescent radiation to occur such that it passes through a filter 16 to a tube lens 17, such that, as a whole, the fluorescent sample 7 is imaged onto the detector 5.

For the purpose of controlling the operation of the microscope 6, a control device is provided, formed here as a computer 18 having a display 19 and keyboard 20. The method steps S2 to S6 are effected in the computer 18. The frame rate of the matrix detector is crucial for the total measurement time, such that a matrix detector 5 having a frame rate that is as high as possible is advantageous for reducing the measurement time.

By means of the microscope 6, the method described realizes a complete image that, for example, has a spatial resolution increased by a factor of 10 in comparison with the optical resolution of the microscope. The optical resolution of the microscope 6 can be, for example, 250 nm laterally and 500 nm axially.

Figure 6:
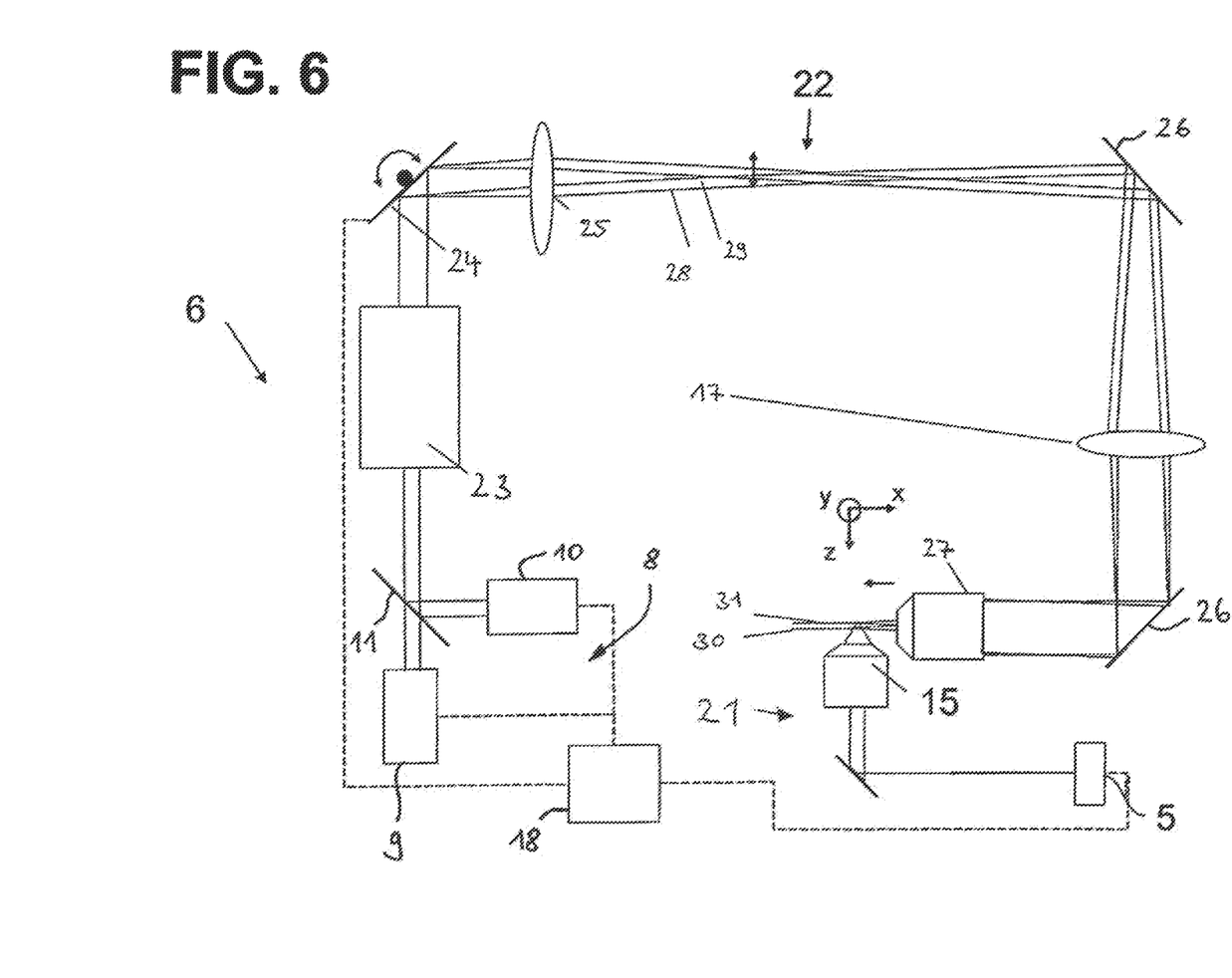
FIG. 6 is a schematic representation of a microscope for PAL microscopy with high resolution also in the depth direction, in a first design.

The procedure described above, or the microscope that has been explained, achieves high resolution, i.e. an optical resolution which is increased above the diffraction limit, in a plane perpendicular to the incident radiation. In order then to achieve a high resolution along the direction of incidence also, i.e. in the depth direction (usually referred to as the z coordinate), the illumination of the sample with excitation or activation radiation, the illumination being represented merely schematically in FIG. 5, is realized such that it alternately illuminates two differing depth regions of the sample, which are located behind one another in the depth direction and which overlap. An exemplary structure for this is shown by FIG. 6. Elements that have already been explained in respect of their structure or function are provided with the same reference numbers as in FIG. 5, such that the description thereof need not be repeated over again.

The illumination beam path 22 is now formed such that the illumination is introduced laterally, in the form of a light sheet, into the sample. For this purpose, the radiation source 8 feeds a radiation adaptation system 23, which directs the radiation onto an adjustable mirror 24, usually a galvo-scanner. The latter is swivelled, e.g. between two positions, and directs the thus differentially deflected radiation to a scanning objective lens 25. There is then a beam path, which is deflected, for example, into two differing positions 28 and 29, depending on the position of the mirror 24. The beam adaptation system 23 can include, for example, a cylindrical lens, which is used to shape the light sheet. Moreover, zoom lens system elements, which adapt the light sheet in respect of its extent in the z and y directions, can be arranged here. In addition, intensity-regulating elements (AOTF, filters) can be provided, which allow regulation of the beam intensity. The mirror 24 can also be realized as a mirror group that, behind the scanning objective lens 25, allows a beam deflection not only into the positions 28 and 29 (parallel to the plane of drawing), but also into positions perpendicular to the plane of drawing. In such a design, it is also possible to dispense with a cylindrical lens, since the light sheet is produced, as it were, by a time-based scanning in the y direction. The scanning takes place at a faster speed than the time resolution of the detection process.

Via a deflecting mirror 26, the tube lens 17 and a further deflecting mirror 26, the radiation reaches an illumination objective lens 27, which introduces the radiation into the sample (which is not represented) perpendicularly in relation to the depth direction of the sample imaging, i.e. in an x/y plane. The coordinate system is indicated, by way of example, in FIG. 6. Two light sheets 30, 31, which illuminate the sample, for example, with excitation radiation, are thereby obtained for two positions of the adjustable mirror 24.

Figure 7:
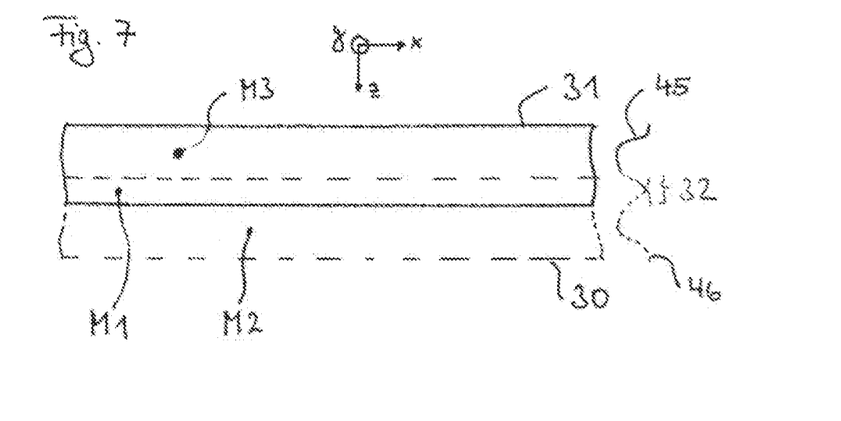
FIG. 7 is a schematic sectional representation of an illumination in the microscope of FIG. 6.

The light sheets 30 and 31 are represented in enlarged form in FIG. 7. They are offset in the z direction in relation to one another. Each light sheet has an intensity distribution in the z direction. In actuality, the light sheets 30 and 31 are very elongate beam waists; for simplification, this waist is represented in FIG. 7 by parallel delimitation of the light sheet. The intensity distribution 46 of the light sheet 30 then overlaps with the intensity distribution 45 of the light sheet 31, such that there is an overlap 32. In this overlap 32, the sample is illuminated by both light sheets when the light sheets 30 and 31 are switched on and off alternately.

Figure 8:
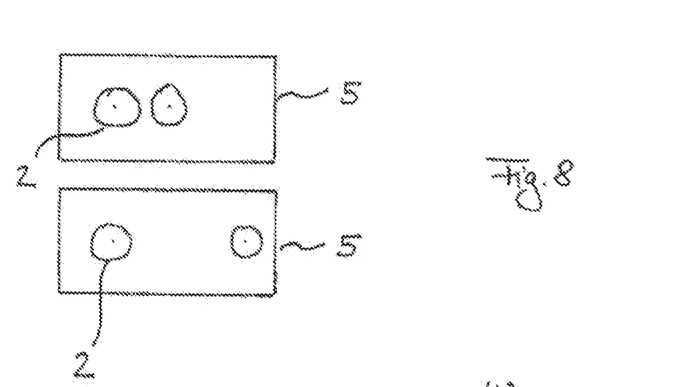
FIG. 8 depicts top views of the detector of the microscope of FIG. 6.

This has the result, as represented in FIG. 8, that only marking molecules located in this overlap 32 exhibit fluorescent radiation in the case of both illumination states, i.e. both when the light sheet 30 is switched on and when the light sheet 30 is switched off and the light sheet 31 is activated. This is indicated schematically in FIG. 8. The figure shows a top view of the image plane of the detector 5. In the upper image of FIG. 8, the light sheet 31 is switched on and the light sheet 30 is switched off. In the lower top view of the detector 5, on the other hand, the light sheet 30 is activated and the light sheet 31 is dark. As can be seen, a diffraction disc appears in both images only in the case of a marking molecule M1, which is indicated in FIG. 7 in the overlap 32 of the light sheets 30 and 31. A marking molecule M2, which is located in the light sheet 30, but below the overlap 32, appears only in the lower image. A marking molecule M3, which, on the other hand, is located only in the light sheet 31, can be seen only in the upper image.

The distance between the light sheets can be adjusted through appropriate setting of the angular difference of the two tilt positions of the adjustable mirror 34. Since, at the same time, the thickness of the light sheets in the z direction is known, the size of the overlap 32 in the z direction can be adjusted in this way. Consequently, even in the case of typical light-sheet thicknesses of 1 μm, it is possible to obtain a very much more accurate specification of the depth position of a luminescent marking molecule. The resolution in the depth direction is associated with the extent of the overlap 32 in the z direction. As is yet to be explained in the following, there are also possibilities for increasing the resolution yet more.

Figures 9, 10:
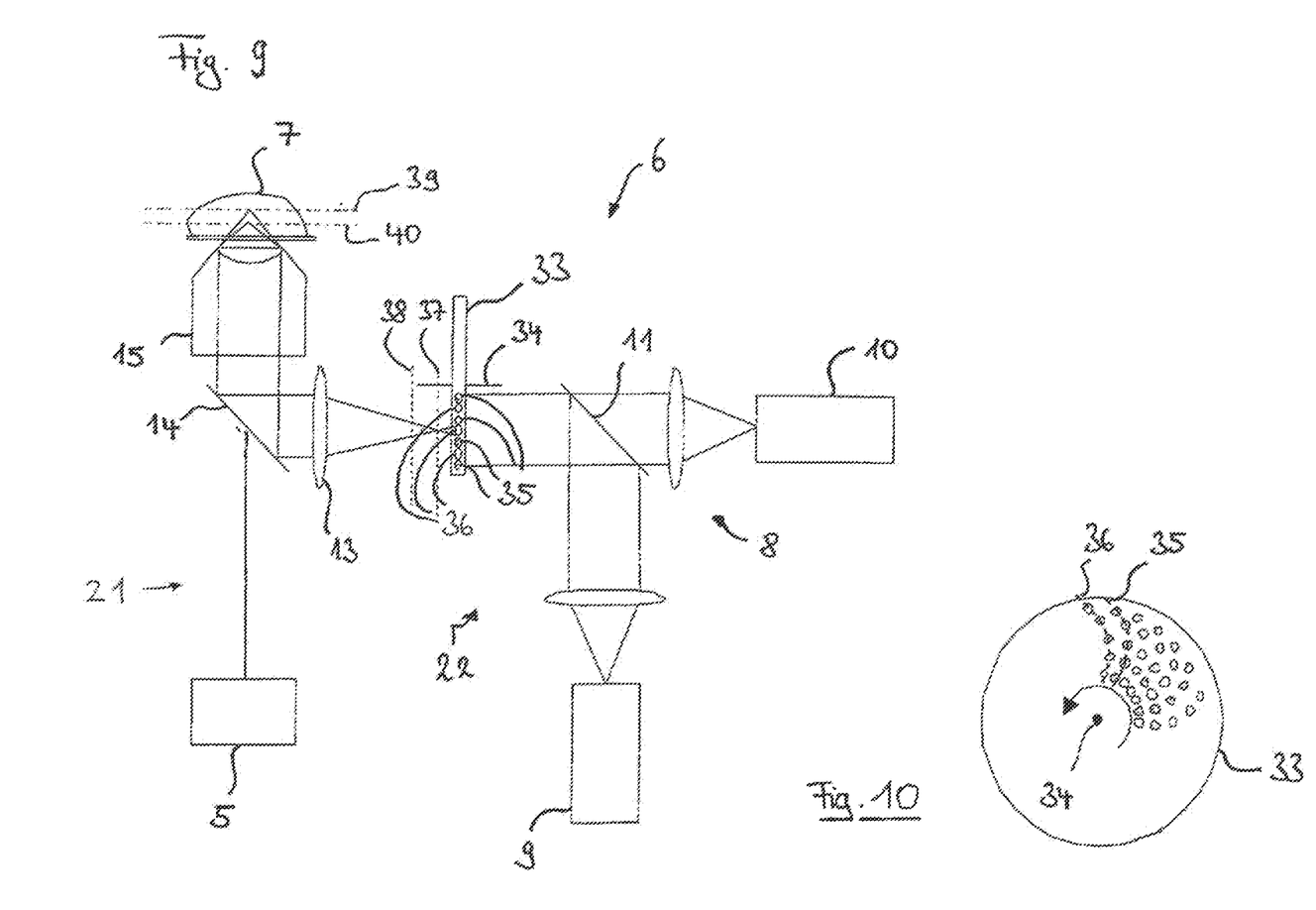
FIG. 9 is a schematic representation of a microscope according to a second design.
FIG. 10 is a top view of a mini-lens rotary disc used in the microscope according to FIG. 9.

FIG. 9 shows a microscope 6 of a further design, which likewise achieves a depth resolution in the case of PAL microscopy. In the design of FIG. 9, the depth of field regions of the illumination, which are located behind one another and overlap, are produced by means of excitation radiation, with the illumination beam path 22 in a reflected-light configuration. Arranged in the illumination beam path 22, which is formed in a manner similar to that of FIG. 6, there is a mini-lens rotary disc 33, which rotates about an axis 34 located outside of the optical axis. On the mini-lens rotary disc 33, which, by its function in the beam path, corresponds to a known Nipkov disc, there are mini-lenses 35, 36, instead of the holes provided in the Nipkov disc. Mini-lenses 35 of a first focal length alternate with mini-lenses 36 of a second focal length. The differing focal lengths ensure that the sample is illuminated with radiation in two differing focal planes 37, 38, which are spaced apart along the optical axis, as a result of which, in the sample, the foci are likewise coupled into two focal planes, which are now spaced apart in the depth direction.

FIG. 10 shows a top view of the mini-lens rotary disc 33 and the arrangement of the mini-lenses 35, which have a first focal length, and the mini-lenses 36 having a second focal length.

Figure 11:
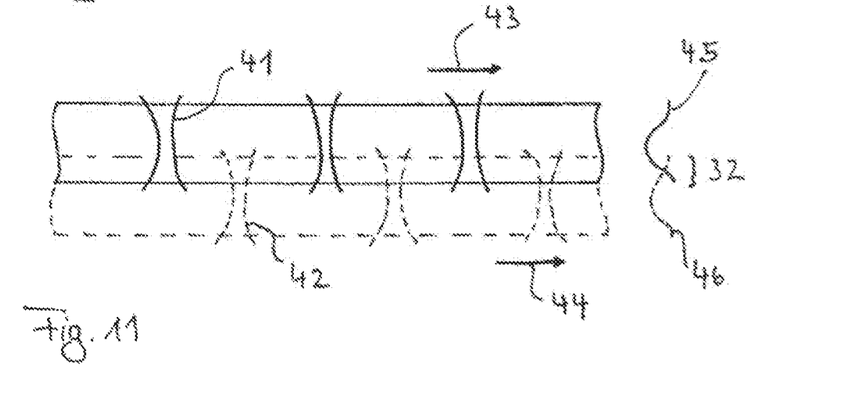
FIG. 11 is a representation similar to that of FIG. 7, but for the microscope of FIG. 9.

The effect of this structure, or the illumination achieved thereby, is represented schematically in FIG. 11. It can be seen that a plurality of foci 41 pass through the sample in the focal plane and in the direction of an arrow 43. Synchronously, and with a time offset in relation thereto, foci 46 pass through parallelwise in relation thereto, i.e. in the direction of the arrow 44, in the focal plane. Since each focus has an intensity distribution, which is indicated schematically at 45 for the foci 41 and at 46 for the foci 42, an overlap 32 is again obtained as a result.

In the embodiment of FIG. 9, the overlap 32 is predefined by the mini-lens rotary disc 33. In addition, the beam splitter 14 in the illumination beam path can be preceded by a zoom lens system, which likewise makes it possible to set the offset between the focal planes and, consequently, the overlap region 32. In terms of detection, the design of FIG. 9 achieves a simultaneous illumination in the focal planes, since the foci travel along the arrows 43, 44 considerably faster than could be resolved by the detection process.

The mini-lens rotary disc is usually constructed such that, per revolution, z (e.g. 12) images are scanned, i.e. z recurrent lens arrangements are arranged on the disc. Image recording is synchronized to the rotation of the disc such that exactly 1 to n scanning operations by disc rotation coincide with recording of an image. In this case, n is a whole-number part of z. For the case that exists here, every second of the recurrent lens arrangements, for example, (or, depending on an anticipated camera frame rate, also, for example, the second 6 of 12, etc.) has a different focal length; in the case of synchronization similar to that above, it is thus achieved that, in each case, one image is recorded with illumination "above" and one with illumination "below"; the corresponding assignment of the images to the illumination states is thus achieved.

The production of sample regions, located behind one another, by scanning with foci bundled in focal planes that are spaced apart has the advantage, not only that a reflected-light illumination configuration can be selected, but preferably also makes possible a development to the effect that the coupled-in radiation, for example the excitation radiation, utilizes a 2-photon effect. As is known, such an effect sharpens the intensity distribution by squaring and allows the overlap 32 to be set with precision to a very small dimension. Accordingly, the localization in the depth direction is also highly precise. In addition, sample regions not intended for the imaging operation are not subjected to radiation load, which, as is known, could result in bleaching of marking molecules, etc.

Figure 14:
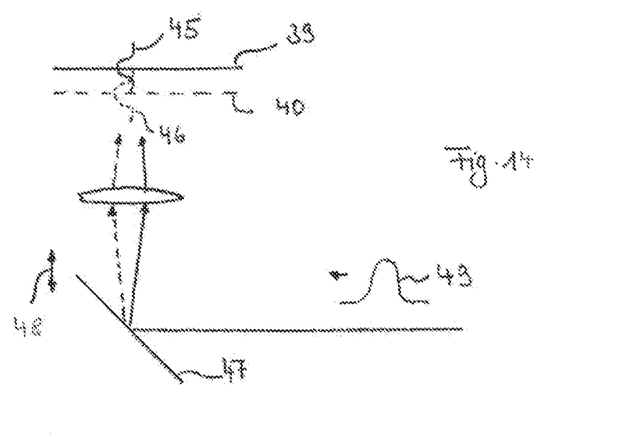
FIG. 14 is a schematic representation of a microscope according to a third design.

In a further design, the production of two differing depth of field regions that are staggered in the depth direction can also be performed by using a diffractive element (DOE), which is imaged into the sample. This is shown schematically in FIG. 14. The diffractive optical element 47 is subjected to a displacement 48. At the same time, it is irradiated with an initial intensity distribution 49. Depending on the displacement 48, the corresponding focal plane, which is achieved by means of the diffractive optical element 47, is displaced in the z direction, such that, again, the focal planes are obtained for the intensity distributions 45 and 46 then present.

The localization in the depth direction can already be effected in that molecules that are not located in the overlap 32 are separated out, since they appear only in one of the two images, i.e. only for one of the two illumination states. The spatial resolution is then defined substantially by the extent of the overlap 32.

Figure 12:
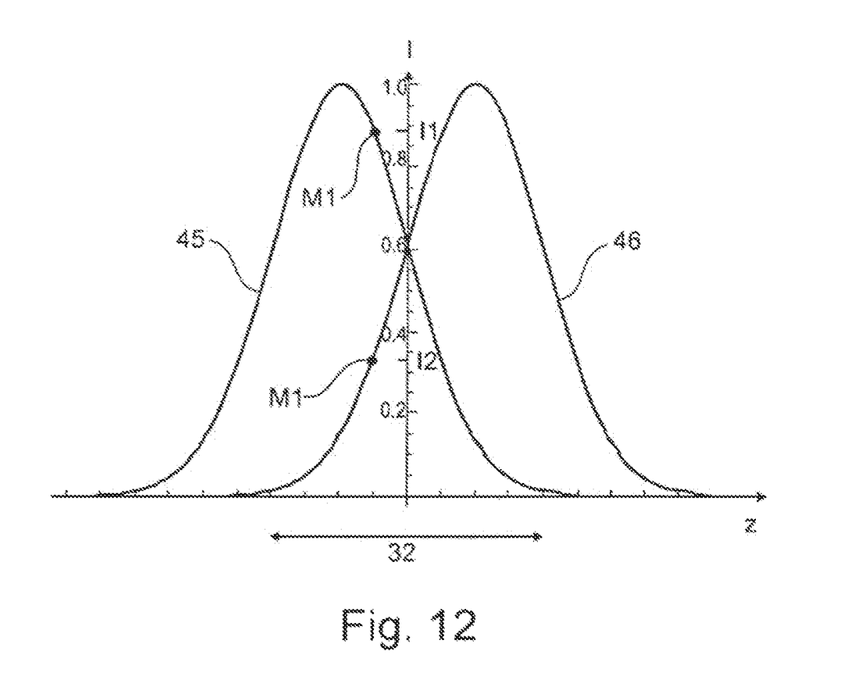
FIGS. 12 and 13 are diagrams to explain the isolation of luminescent marking molecules in the depth direction.

In a development, it is possible to further increase the spatial resolution. For this, use is made of the fact that the luminescence intensity increases with the excitation intensity. This allows the intensity distribution of the two illumination states to be utilized. FIG. 12 shows the intensity distributions 45 and 46 along the depth direction (z coordinate). The intensity I of the intensity distributions 45 and 46 overlap each other in the overlap 32. A marking molecule M1 located in this region is recorded with a first intensity I1 if it is excited, by the illumination state with the intensity distribution 45, to emit luminescent radiation. If, on the other hand, it is illuminated with the illumination state according to the intensity distribution 46, the detector 5 perceives the marking molecule M1 with the intensity I2. Owing to the position of the marking molecule M1, which is outside of the centre of the overlap region, I1 is lower. For this reason, optionally, the intensity differences of an excited marking molecule are used for determination of the depth position.

Figure 13:
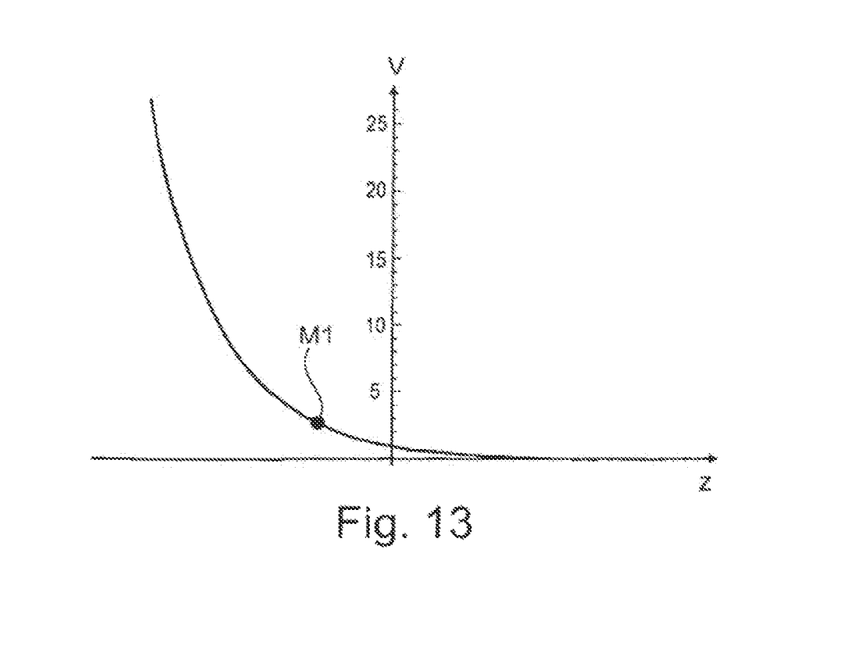

A possible procedure is given by FIG. 13. There, the ratio of the intensities I1 and I2 is plotted as a function of the z coordinate. It can be seen that the depth coordinate for the molecule M1 can be specified with a resolution that is very much smaller than the dimension of the overlap 32. Naturally, instead of ratio formation, it is also possible to use another type of evaluation of the intensity differences between I1 and I2.

It may also be mentioned that, in the case of time-based differentiation of the two excitation regions, the excitation intensity can also be varied adaptively from one region to the other, and the change in the excitation intensity is included in the evaluation. This can be advantageous in order to obtain a better noise statistic, or to increase the entire dynamic range of the measurement.

Figure 15:
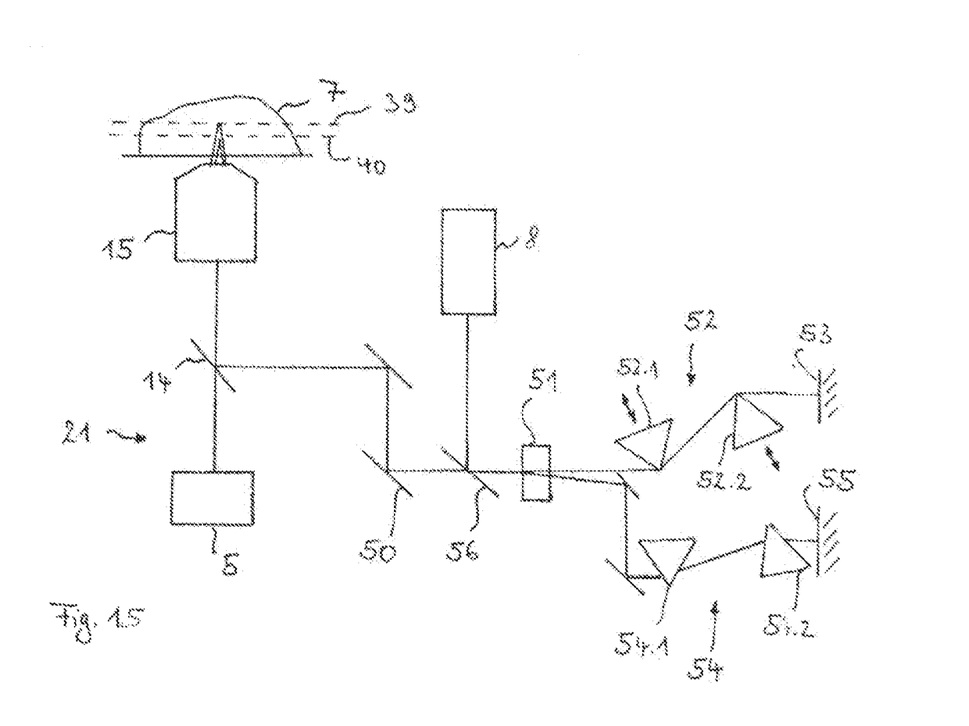
FIG. 15 is a schematic representation of a microscope according to a fourth design.

A further possibility for producing the two illumination states in differing z positions in the sample is represented schematically in FIG. 15. Here, two beam paths, having a differing dispersion of the group velocity, are provided in the illumination beam path. These two beam paths are realized by means of prism pairs 52 and 54. The radiation from the radiation source 9 is switched back and forth between the prism pairs 52 and 54 via a beam splitter 56 and an AOTF 51, which in this case is an example of a switching element. In each of the two beam paths, the radiation passes through a prism pair 52.1 and 52.2, or 54.1 and 54.2, is reflected at an end mirror 53 or 55, and reaches the beam splitter 14 via a grating 50. The differing dispersions of the group velocities result, in the imaging via the grating 50, in the two differing focal planes in the sample 7.

The changeover between the two focal planes is again effected synchronized with the image recording in the detection beam path 21. The optional displaceability of the prism pair 52 allows the dispersion difference to be set.

The detection of the two images that are assigned to the two illumination states can be performed by means of a camera, which is read out in a correspondingly synchronized manner. To accelerate the method, it is advantageous to reflect two cameras into the detection beam path, via a corresponding beam splitter. In particular, the dead time that usually occurs during the camera read-out can thereby be reduced.

The principle of providing differing illumination states having depth of field regions that differ in the depth position and that overlap is, naturally, not limited to two states. Naturally, it is also possible to use a plurality of depth regions, located behind one another, which overlap in pairs and/or are modulated with differing modulation frequency. The same applies, naturally, in respect of the switching between the regions. Exclusive switching on and off need not be performed. It is also perfectly possible to modulate the illumination regions with differing modulation frequencies. The depth position is then obtained from the beat signal, e.g. by means of a lock-in detection.

Moreover, the production of the light sheet can be combined with the so-called Bessel SPIM technique, as known from Fahrbach, F. O., Rohrbach, A., "A line scanned light-sheet microscope with phase shaped self-reconstructing beams", Optics Express 24229, vol. 18, no. 23, 2010.

For the various embodiments, the following developments are considered, or the following advantages apply:

For the switching between the illumination states, particularly in the case of the lateral illumination by means of a light sheet, galvanometer scanners, acousto-optic modulators or filters and/or switchable phase elements come into consideration.

The image recording or evaluation is matched to the differing illumination states. This can be effected by synchronization. Frequency evaluating approaches are also possible, however, with the two illumination states being differentially modulated, particularly with respect to time.

The embodiments described improve the penetration depth of the microscopic imaging, which, in the case of conventional PAL microscopy with TIRF illumination, is limited to the immediate sample boundary layer. High-resolution, three-dimensional imaging is achieved. At the same time, the contrast is improved by suppression of a background signal originating outside of the focus region. The three-dimensional increase in resolution is achieved in that the localization method also acts in the z direction.

As an alternative to the approaches described above, with a displacement of the plane of the illumination, it may be pointed out that it is ultimately only a matter of a relative displacement of the illumination plane in the sample. Naturally, this can also be realized by a suitable movement of the sample.

The procedure explained achieves not only more rapid image recording; in the z direction, the point spread function, which is well known for a standard objective lens, results at the same time in a better acquisition of images in the localization process. In particular, there is no difference of the point spread function in the z direction and in the x/y direction, since the astigmatic lenses, etc. that are described in the state of the art for high-resolution 3D microscopy are not required.

The illumination intensity can be adjusted and, in particular, readjusted during image recording. It is thereby possible to achieve a situation such that the signal-to-noise ratio does not vary at differing regions of the sample.

In the case of the use of a light sheet, the distribution of the intensity in the z direction of the imaging can be modified in order to structure the light sheet in this direction. A negative image of the sample can thereby be obtained. It is also possible to make better use of saturation effects.

An interferometric superimposition of differing light sheets or illumination states also comes into consideration for producing the illumination states that are differently structured in the z direction.

The procedure explained additionally makes possible the evaluation of cross-correlations between signals at differing sample locations.

The invention claimed is:

1. A microscope for high-resolution luminescence microscopy of a sample marked with marking molecules that can be activated in such a manner that, once activated, the marking molecules can be excited to emit particular luminescent radiation, wherein the microscope comprises:
   a) an illumination beam path formed for repeated activation and excitation of a subset of the marking molecules to emit luminescent radiation at least some of the luminescent marking molecules at least at a distance from the luminescent marking molecules immediately adjacent thereto greater than or equal to a minimum resolvable length which results from a predetermined optical resolution;
   b) an imaging device including an objective and a detector, the imaging device being configured to repeatedly image the sample along a depth direction and with the predetermined optical resolution;
   c) a control and evaluation device, including a computer, operably coupled to the imaging device and programmed with an algorithm that produces individual images based on data received from the imaging device and determines the geometrical locations of the luminescent marking molecules in the individual images with a spatial resolution which is increased above the predetermined optical resolution; wherein
   d) the illumination beam path introduces the activation and/or excitation radiation into at least two regions, the regions each extending along a plane substantially perpendicular to the depth direction, the regions having a predetermined extent in the depth direction, and the regions arranged in such a manner that said regions are one behind another in the depth direction and overlap only partially; and wherein
   e) the imaging device is configured to capture separate images of the sample for activation and/or excitation of each of the at least two regions and the control and evaluation device obtains a depth information relating to the marking molecules from the separate images.

2. The microscope according to claim 1, wherein the illumination beam path introduces the activation and/or excitation radiation in the form of at least one light sheet that lies transversely in relation to the depth direction and the thickness of which defines the extent, the thickness of the light sheet being diffraction-limited.

3. The microscope according to claim 2, wherein the illumination beam path includes an optical element that displaces the light sheet, transversely in relation to the depth direction, into at least two positions.

4. The microscope according to claim 2, wherein the illumination beam path has two spaced-apart light sheets, the light sheets being switched on and off alternately or differentially modulated.

5. The microscope according to claim 2, wherein the illumination beam path focuses the activation and/or excitation radiation along the depth direction into two light sheets that each lie transversely in relation to the depth direction in two respective planes, each of the two respective planes being oriented transversely to the depth direction, focuses a first focus of a pair of diffraction-limited foci into a first of the two planes and focuses a second focus of the pair of diffraction-limited foci into a second of the two planes, and displaces the foci along the two respective planes in order to form the two regions, wherein the depth of field of the focussing defines the extent of the regions.

6. The microscope according to claim 5, wherein the illumination beam path comprises a mini-lens array arranged on a rotating disc.

7. The microscope according to claim 3, wherein the optical element that displaces the light sheet comprises a scanning mirror.

8. The microscope according to claim 3, wherein the optical element that displaces the light sheet comprises a Nipkov disc.

9. The microscope according to claim 3, wherein the optical element that displaces the light sheet comprises a diffractive optical element.

10. The microscope according to claim 3, wherein the optical element that displaces the light sheet comprises a combination of prisms.

* * * * *